US011535256B2

(12) United States Patent
Ghannam et al.

(10) Patent No.: US 11,535,256 B2
(45) Date of Patent: Dec. 27, 2022

(54) CHIONOPHOBIA INTERVENTION SYSTEMS AND METHODS

(71) Applicant: Ford Global Technologies, LLC, Dearborn, MI (US)

(72) Inventors: Mahmoud Yousef Ghannam, Canton, MI (US); Rajarshi Roychowdhury, Dearborn, MI (US); John Robert Van Wiemeersch, Novi, MI (US); Brian Bennie, Sterling Heights, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 224 days.

(21) Appl. No.: 17/064,093

(22) Filed: Oct. 6, 2020

(65) Prior Publication Data
US 2022/0105944 A1    Apr. 7, 2022

(51) Int. Cl.
*B60W 40/02* (2006.01)
*G06F 3/16* (2006.01)
(Continued)

(52) U.S. Cl.
CPC .............. *B60W 40/02* (2013.01); *A61B 5/165* (2013.01); *A61B 5/18* (2013.01); *A61B 5/6893* (2013.01);
(Continued)

(58) Field of Classification Search
CPC ...... B60W 40/02; B60W 30/09; B60W 30/14; B60W 40/08; B60W 50/06; B60W 50/14; B60W 2555/20; B60W 2540/221; B60W 2050/146; B60N 2/976; B60N 2/5678; A61B 5/165; A61B 5/18; A61B 5/6893; B60K 35/00; B60K 2370/1529;
(Continued)

(56) References Cited

U.S. PATENT DOCUMENTS 9,429,943 B2 *  8/2016  Wilson ................. G05D 1/0246
10,836,348 B1 * 11/2020  Papworth ............ H04L 12/2827
(Continued)

FOREIGN PATENT DOCUMENTS

JP    2019131096 A    8/2019

OTHER PUBLICATIONS

Fritscher, L., et al., "The Fear of Winter Driving in the Snow," American Psychiatric Association (2013). Diagnostic and Statistical Manual of Mental Disorders (5th Ed.) (2 pages).
(Continued)

*Primary Examiner* — Fadey S. Jabr
*Assistant Examiner* — Naeem Taslim Alam
(74) *Attorney, Agent, or Firm* — Frank Lollo; Eversheds Sutherland (US) LLP

(57) ABSTRACT

Chionophobia intervention systems and methods are disclosed herein. An example method includes detecting snowfall from a vehicle sensor of a vehicle or a service provider, displaying a prompt on a human machine interface (HMI) to query a user regarding additional assistance in response to the detection of the snowfall, activating a first stage response after detecting the snowfall, determining when the first stage response is insufficient based on feedback received from the user, and activating a second stage response when the feedback received from the user indicates that the first stage response is insufficient.

18 Claims, 3 Drawing Sheets

(51) Int. Cl.
*G06F 3/14* (2006.01)
*B60W 30/14* (2006.01)
*B60W 30/09* (2012.01)
*B60Q 1/06* (2006.01)
*B60W 50/06* (2006.01)
*B60N 2/90* (2018.01)
*B60W 50/14* (2020.01)
*B60N 2/56* (2006.01)
*B60K 35/00* (2006.01)
*B60W 40/08* (2012.01)
*A61B 5/16* (2006.01)
*A61B 5/18* (2006.01)
*A61B 5/00* (2006.01)
*G06T 11/00* (2006.01)

(52) U.S. Cl.
CPC ............ *B60K 35/00* (2013.01); *B60N 2/5678* (2013.01); *B60N 2/976* (2018.02); *B60Q 1/06* (2013.01); *B60W 30/09* (2013.01); *B60W 30/14* (2013.01); *B60W 40/08* (2013.01); *B60W 50/06* (2013.01); *B60W 50/14* (2013.01); *G06F 3/14* (2013.01); *G06F 3/165* (2013.01); *G06T 11/00* (2013.01); *B60K 2370/157* (2019.05); *B60K 2370/1529* (2019.05); *B60W 2050/146* (2013.01); *B60W 2540/221* (2020.02); *B60W 2555/20* (2020.02)

(58) Field of Classification Search
CPC ....... B60K 2370/157; B60Q 1/06; G06F 3/14; G06F 3/165; G06T 11/00
See application file for complete search history.

(56) References Cited

U.S. PATENT DOCUMENTS

| | | | |
|---|---|---|---|
| 2011/0298638 A1* | 12/2011 | Groeneweg | G08G 1/096775 340/905 |
| 2014/0222272 A1 | 8/2014 | Raste et al. | |
| 2015/0302718 A1 | 10/2015 | Konigsberg | |
| 2016/0023602 A1* | 1/2016 | Krishnan | G02B 27/017 348/115 |
| 2016/0280134 A1* | 9/2016 | Miura | G08G 1/04 |
| 2016/0303968 A1* | 10/2016 | Miller | B60K 35/00 |
| 2017/0132482 A1* | 5/2017 | Kim | G06V 20/586 |
| 2017/0141461 A1* | 5/2017 | Van Dan Elzen | H05B 3/145 |
| 2017/0323262 A1* | 11/2017 | Hillis | G06Q 10/0834 |
| 2017/0355377 A1* | 12/2017 | Vijaya Kumar | B60W 50/0098 |
| 2017/0364069 A1* | 12/2017 | Colella | H04W 4/02 |
| 2018/0244288 A1* | 8/2018 | Glaser | B60W 50/14 |
| 2018/0281770 A1* | 10/2018 | Chen | G07C 5/008 |
| 2018/0322775 A1* | 11/2018 | Chase | H04W 4/44 |
| 2019/0248380 A1 | 8/2019 | Tatourian et al. | |
| 2019/0287290 A1* | 9/2019 | Sakthivel | G06T 15/06 |
| 2019/0291740 A1* | 9/2019 | Higashitani | G01S 17/931 |
| 2019/0339519 A1* | 11/2019 | Toki | B60K 35/00 |
| 2021/0178959 A1* | 6/2021 | Ishida | F21S 41/151 |
| 2021/0191399 A1* | 6/2021 | Verghese | G08G 1/0112 |
| 2021/0300259 A1* | 9/2021 | Shibata | B60Q 9/008 |

OTHER PUBLICATIONS

Search Report—www.anovip.com. (22 pages).

* cited by examiner

CHIONOPHOBIA INTERVENTION SYSTEMS AND METHODS

BACKGROUND

According to a study carried out by the American Meteorological Society, chionophobia, or intense fear of snow, is the second most prevalent natural environment phobia subtype after tornados. People with chionophobia often understand that their fear is unfounded; however, they are unable to control it. Drivers or passengers (e.g., users) who have chionophobia may act in unpredictable ways when driving a car under heavy snowfall. If the user is a passenger, he or she might stress the driver when it is snowing, and this may be a potential hazard for everyone on the road. Like all phobias, the fear of snow may cause a variety of symptoms. Paying undue attention to weather reports, refusing to leave home during snowy weather, and experiencing panic attacks are extremely common in people with chionophobia. For people with acute chionophobia, the mere forecast of a winter storm or snowfall can induce physiological symptoms of fear and anxiety-like cold sweats, panic attacks, and even an unrealistic feeling of doom and dread.

Chionophobia can be driven by an irrational fear of snow that is typically linked to a fear of bodily harm or death. The fear of becoming snowbound and the fear of being stranded in the snow are example manifestations of chionophobia. Unfortunately, both of these situations can be common in parts of the world which experience heavy snowfall. In summary, a user suffering from chionophobia can be a potential hazard to people on the road, could hamper his/her daily activities if the user stays in a region which sees heavy snowfall, and can also hamper future ride-sharing opportunities (other users might not understand the problem the person with chionophobia is facing and might want to cancel the ride out of fear or just being unaware of this problem).

BRIEF DESCRIPTION OF THE DRAWINGS

The detailed description is set forth regarding the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

The present disclosure is generally directed to systems and methods that provide intervention measures during instances of anxiety or fear caused by chionophobia when a user is operating a vehicle. A vehicle of the present disclosure can be configured to detect or infer the presence of snowfall around the vehicle. The vehicle can also be configured to determine when a user is or may be experiencing a negative emotional or physical response due to chionophobia. The negative emotional or physical response can be determined by a connected vehicle from a health record, from information offered by a vehicle user, or from a sensor output.

Once the user is determined to be susceptible to chionophobia (or is experiencing a negative emotional or physical response) and snowfall is detected around their vehicle, the systems and methods can mitigate, reduce, or eliminate this chionophobia using a two-stage interventional approach. In general, the first stage includes indirect or limited intervention techniques. The second stage may include both first stage techniques, along with more direct and complex techniques. A plurality of intervention techniques can be used in combination. In some instances, when chionophobia cannot be remedied by this two-stage approach, a ride-hail service or emergency response service can be dispatched to the location of the vehicle.

Illustrative Embodiments

Figure 1:
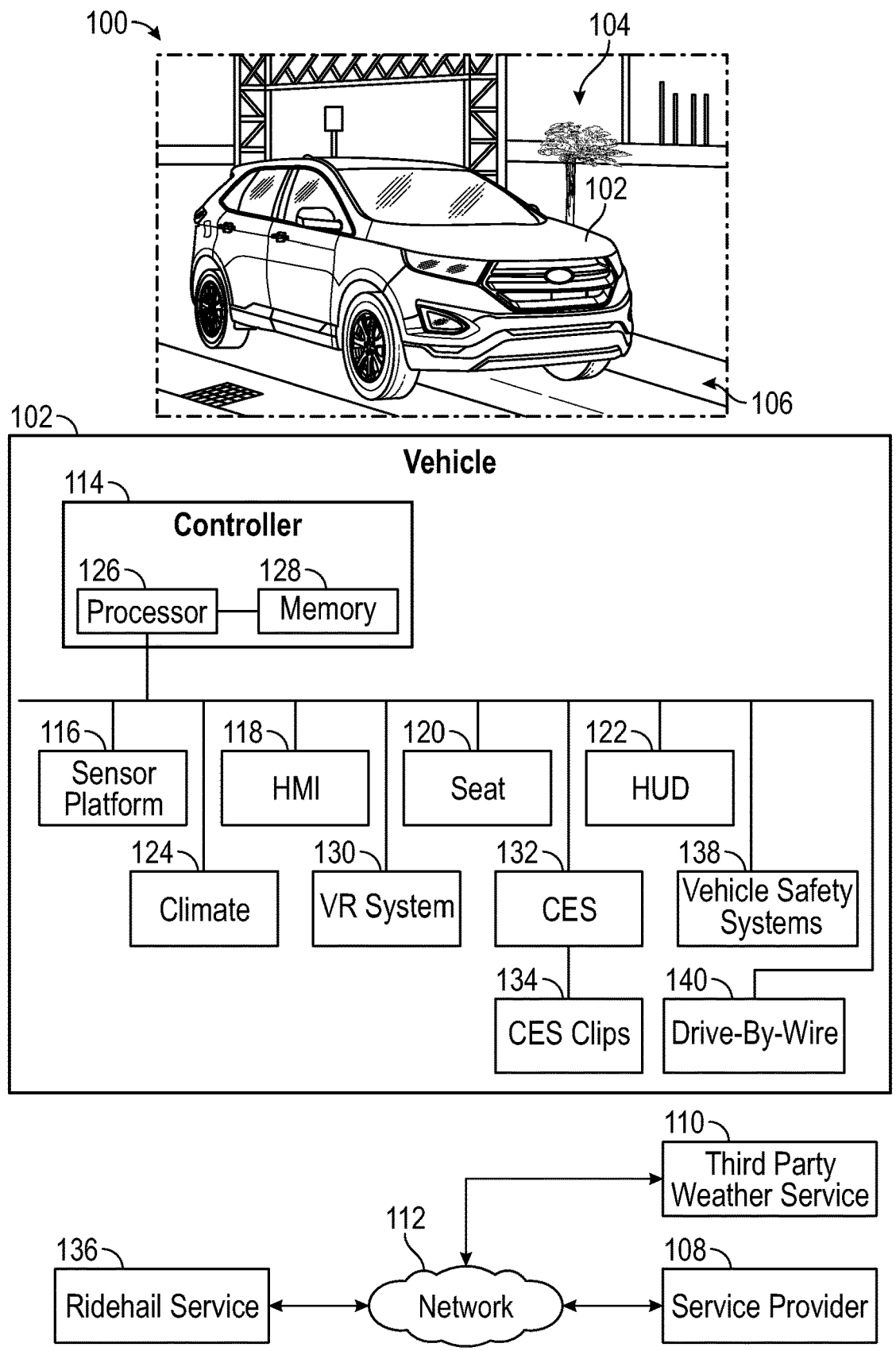
FIG. 1 depicts an illustrative architecture in which techniques and structures for providing the systems and methods disclosed herein may be implemented.

Turning now to the drawings, FIG. 1 depicts an illustrative architecture 100 in which techniques and structures of the present disclosure may be implemented. The architecture 100 can include a vehicle 102 that is operating in an environment 104 where snowfall 106 is present or is likely to be present. The architecture 100 can include a service provider 108, a third-party weather resource 110, and a network 112. The network 112 may include any one or a combination of multiple different types of networks, such as cable networks, the Internet, cellular networks, wireless networks, and other private and/or public networks. In some instances, the network 112 may include cellular, Wi-Fi, Ultra Wide-Band (UWB), C-V2X networks, or Wi-Fi direct. In other embodiments, components of the environment can communicate using short-range wireless protocols. Example protocols include, but are not limited to, Bluetooth®, near-field (NFC), infrared, and the like.

The vehicle 102 can comprise a controller 114, a sensor platform 116, a human-machine interface (HMI) 118, a seat 120, a heads-up display (HUD) 122, and a climate control system 124. Generally, the controller 114 can comprise a processor 126 and memory 128. The memory 128 stores instructions that can be executed by the processor 126 to perform any of the two-stage intervention methods disclosed herein. The controller 114 can be configured to communicate over the network 112 with any of the components of the architecture such as the service provider 108 and the third-party weather resource 110. The controller 114 can incorporate or use any vehicle communication device to transmit and/or receive data over the network 112.

Generally, the vehicle 102 may take the form of another passenger or commercial automobile such as, for example, a car, a truck, a sport utility, a crossover vehicle, a van, a minivan, a taxi, a bus, etc., and may be configured and/or programmed to include various types of automotive drive systems. Example drive systems can include various types of internal combustion engine (ICE) powertrains having a gasoline, diesel, or natural gas-powered combustion engine with conventional drive components such as, a transmission, a drive shaft, a differential, etc. In another configuration, the vehicle 102 may be configured as an electric vehicle (EV). More particularly, the vehicle may include a battery EV (BEV) drive system, or be configured as a hybrid EV (HEV) having an independent onboard powerplant, a plug-in HEV (PHEV) that includes a HEV powertrain connectable to an external power source, and/or includes a parallel or series hybrid powertrain having a combustion engine powerplant and one or more EV drive systems. HEVs may further include battery and/or supercapacitor banks for power storage, flywheel power storage systems, or other power generation and storage infrastructure. The vehicle may be further configured as a fuel cell vehicle (FCV) that converts liquid or solid fuel to usable power using a fuel cell, (e.g., a hydrogen fuel cell vehicle (HFCV) powertrain, etc.) and/or any combination of these drive systems and components.

Further, the vehicle 102 may be a manually driven vehicle, and/or be configured and/or programmed to operate in a fully autonomous (e.g., driverless) mode (e.g., level-5 autonomy) or in one or more partial autonomy modes. Examples of partial autonomy modes are widely understood in the art as autonomy Levels 0 through 5. A vehicle having a Level-0 autonomous automation may not include autonomous driving features. An autonomous vehicle (AV) having Level-1 autonomy may generally include a single automated driver assistance feature, such as steering or acceleration assistance. Adaptive cruise control is one such example of a Level-1 autonomous system that includes aspects of both acceleration and steering. Level-2 autonomy in vehicles may provide partial automation of steering and acceleration functionality, where the automated system(s) are supervised by a human driver that performs non-automated operations such as braking and other controls. Level-3 autonomy in a vehicle can generally provide conditional automation and control of driving features. For example, Level-3 vehicle autonomy typically includes "environmental detection" capabilities, where the vehicle can make informed decisions independently from a present driver, such as accelerating past a slow-moving vehicle, while the present driver remains ready to retake control of the vehicle if the system is unable to execute the task. Level-4 autonomy includes vehicles having high levels of autonomy that can operate independently from a human driver, but still include human controls for override operation. Level-4 automation may also enable a self-driving mode to intervene responsive to a predefined conditional trigger, such as a road hazard or a system failure. Level-5 autonomy is associated with autonomous vehicle systems that require no human input for operation, and generally do not include human operational driving controls.

Some embodiments disclose the controller 114 as controlling various components of the vehicle. It will be understood that this can include direct control of a component by the controller 114 or indirect control of the component through another controller. For example, the controller 114 could indirectly control vehicle braking or throttling through communication with a drive-by-wire system of the vehicle. The vehicle 102 can also comprise additional components such as a virtual reality system 130 and a cranial electrotherapy system (CES) 132. Specific details regarding these systems will be discussed in greater detail herein.

Broadly, the controller 114 can operate in a surveillance mode to detect when snowfall is present in the environment 104 around the vehicle 102. The controller 114 can also determine when snowfall is predicted or likely to be encountered by the vehicle 102. Snowfall can be determined from the sensor platform 116 onboard the vehicle 102. For example, the sensor platform 116 can include a moisture sensor and/or a temperature sensor, the data output from which can be used by the controller 114 to determine that snowfall is occurring or is likely to occur. The controller 114 can also determine or confirm snowfall based on information obtained from the third-party weather resource 110.

Once snowfall is inferred or determined, the controller 114 can determine if a user, such as a driver or a passenger in the vehicle 102 may be subject to chionophobia. In one example, the controller 114 can present a query through the HMI 118 to the user. The user could confirm or deny if they have chionophobia. The controller 114 can be configured to determine chionophobia of a user from a record such as an electronic health record or health information stored at the service provider 108. In yet other instances, measurements from the sensor platform 116 can be used to determine or infer chionophobia. For example, the sensor platform 116 could include an in-vehicle camera or biometric sensor. A biometric sensor associated with the vehicle (such as a biometric sensor integrated into a steering wheel or the seat 120) can be used to determine that the user has at least one biometric reading that indicates that the user is experiencing stress. The biometric sensor could include a heart rate monitor, pulse sensor, or blood pressure sensor that detects when the user's blood pressure or heart rate is elevated.

In some instances, the biometric sensor may be used to identify a user and compare it to a vehicle or cloud database with a medical record provided previously by the user (or third party) who suffers from chionophobia. Stated otherwise, the vehicle can store or access information that indicates that a user has chionophobia. The biometric data can be used to identify and authenticate the user when environmental conditions are likely to cause the user to experience chionophobia.

In one example, driver state monitoring (DSM) cameras of the sensor platform 116 can be used along with various other interior sensors and cameras to determine when the driver or a passenger is suffering from panic and hypertension, once the snow starts to fall. This fear or anxiety can be determined based on using facial recognition techniques. Images of the user obtained from in-vehicle cameras can be compared using machine learning to detect when the user is experiencing a negative emotion such as fear or anxiety. The controller 114 can query the user about possible chionophobia when the controller 114 has determined that snowfall is present or likely to occur and the user is experiencing a negative emotion. The user can confirm or deny that they are experiencing chionophobia as noted above. All the above methods can be supplemented by prior database records for the user (driver or passenger).

When a user is determined to be in a stress-induced state and snowfall is detected, the controller 114 can initiate one or more mitigation or intervention responses. In general, when known or assumed that the user has chionophobia and that snowfall is likely or is present, the controller 114 can initiate one or more mitigation or intervention responses.

As noted above, chionophobia mitigation/intervention can be responded to using a two-stage approach. For example, the controller 114 can be configured to execute one or more first stage intervention or response techniques. An example stage one intervention could include activating a massaging function associated with the seat 120. Another example stage one intervention could include activating a seat warming function of the seat 120. For example, a heating element(s) associated with the seat 120 can be activated along with the massaging function. An example stage one intervention could include selectively adjusting aspects of the climate control system 124. For example, the temperature in the cabin of the vehicle can be increased to reduce the user's stress response. The vehicle 102 can include an aromatherapy dispenser integrated into the climate control system 124. A calming scent can be dispersed into the cabin of the vehicle 102.

In some instances, the controller 114 can disable a traction control feature of the vehicle 102. It will be understood that disabling of traction control can increase contact with vehicle tires and snow-covered surfaces. To be sure, the disabling of traction control can be used as a second stage intervention in some instances.

As noted above, a constituent part of chionophobia may include fear of being stuck in their vehicle during a snow event. The controller 114 can be configured to disable a fuel economy or STOP/START function that is used to start and stop the engine when the vehicle is stationary. The controller 114 can disable the STOP/START function when a fuel tank level is above a threshold value, such as 75%. The disabling of the STOP/START function may alleviate a user's fears that the engine may not restart after it has been stopped. The user can select to use or cancel this disabling feature in some instances through input into the HMI 118. In yet another example, the controller 114 can cause a navigation service of the vehicle 102 to re-rout the vehicle to avoid snow or areas of heaver snow fall. Snowfall areas can be determined from the third-party weather resource 110.

The HMI 118 can be used as a medium for delivering stage one intervention(s). For example, the HMI 118 could include an infotainment system that can be controlled to output calming music or sounds. Alternatively, the HMI 118 can be controlled to display a natural sunny scene. The controller 114 can cause the HMI 118 to display or audibly output a humorous story or anecdote. In another example, the controller 114 can cause the HMI 118 to engage the user in trivia questions. In some instances, the controller 114 can cause the HMI 118 to selectively adjust interior lighting to provide a soothing, relaxing light. The soothing, relaxing light could include a change in intensity and/or a change in hue.

In another example, when a user in a vehicle is listening the vehicle radio or watching television, and the content of the radio or television program discusses snow, this may trigger a user's chionophobia. The controller 114 can monitor the content of radio or television programs presented to the user. When words that are indicative of snow are detected, the controller 114 can activate a stage one intervention such as changing a radio station or television program. In another related example, the controller 114 can detect when a user who is present in the vehicle discusses snow. The controller 114 can cause the HMI 118 to output a message or other content to redirect the conversation as a stage one intervention. The triggering of a stage one response can be based on the controller 114 determining that a user in the vehicle has chionophobia using any of the chionophobia detection methods disclosed herein.

Another example first stage intervention could include providing the user with a simulated game for mastering vehicle handling, to increase confidence and reduce anxiety. The controller 114 can provide these games through the HMI 118. The nature and complexity of the games may be tailored to those games suitable when driving and those suitable for passengers or when the vehicle is stationary.

Example games can be presented to a driver when the weather is advantageous (e.g., not snowing or raining, but sunny as an example), so that the skills derived from the exercise/game might help the user when it is snowing. The user can play the game to sharpen their focus on the road and the environment around the car is clear from traffic (when the driver is driving on an empty road). The games might also be played when the car is parked and in that case, the steering, brake, and accelerator along with the HMI will act as a driving simulator and a more nuanced practice session can be simulated.

The controller 114 can also cause the HMI 118 to display images or tutorials that remind the user of onboard driver assist features such as blind-spot information system (BLIS), adaptive cruise control, pre-collision assist with auto emergency braking and adaptive headlight functions. Each of these features may increase peace of mind to the nervous user. These features are collectively illustrated as vehicle driver assist features 138.

In yet other instances, the controller 114 can activate a stage one intervention such as conservative calibration, where vehicle braking distances may be increased when an object is detected through the sensor platform 116 of the vehicle (such as ADAS, advanced driver assistance system cameras). The controller 114 can mute or reduce the vehicle's acceleration and/or braking forces to prevent a sense of high gravitational forces by the user. Any of these stage one intervention measures may be provided while also taking into consideration the safety of the occupant (e.g., in terms of the acceleration/braking). Generally, the controller 114 can be configured to control a drive-by-wire system 140 of the vehicle 102, or another equivalent system or component of the vehicle 102 that converts throttle and/or braking input into engine and/or braking system responses.

During stage one intervention periods, the controller 114 can monitor lane assist features of the vehicle driver assist systems 138 aggressively, as well as acceleration and/or braking behaviors of the user (and corresponding operations of the drive-by-wire systems 140) to ensure safety. During the execution of a stage one intervention measure(s), the controller 114 can be configured to determine when the user has reduced anxiety related to their chionophobia. For example, the controller 114 can cause a question to be displayed on the HMI 118. Alternatively, a natural language query could be output by the vehicle 102 through a voice control system associated with the HMI 118. Other sensor input from the sensor platform 116 could also indicate a reduction in the negative emotional response of the user.

When the user responds positively, the controller 114 can maintain the use of stage one intervention. However, when the user responds negatively, the controller 114 can execute one or more stage two intervention(s). In some instances, the controller 114 can continue to use stage one intervention(s) in combination with any of the stage two intervention(s) disclosed.

In one example, the controller 114 can be configured to allow the user to control a massage level of the massage functionalities of the seat 120. These massage functionalities can be controller either through voice command or through the HMI 118.

The controller 114 can be configured to provide an augmented reality experience to a user using the HUD 122. For context, the HUD 122 projects images onto a viewing space of a vehicle windshield in front of the user, such as a driver. In one example, the HUD 122 could project a virtual sunny environment. In another example, the HUD 122 could display or overlay a view of streets or vehicles that obscure snowfall. For example, if a street is covered in snow, the HUD 122 could display a virtual projection of the street without snow, which could illustrate visible landmarks such as street lines, curbs, and so forth, which may be obscured by the snowfall on the street.

An additional second stage intervention could include the controller 114 interacting with the virtual reality system 130 to provide the user with a virtual reality experience intended to reduce chionophobia. The VR experience could be provided when the vehicle 102 is in a stationary or parked configuration. In some examples, the vehicle 102 could be stationary when parked on a side of a road but the vehicle is running, or when the vehicle 102 is stopped at a stop sign or light. The VR experience can simulate a different environment for the user that reduces the user's fear due to falling snow and calms the user down. In some instances, the VR experience can include the use of a VR headset that can communicatively couple with the controller 114. In some instances, a second stage response can include displaying a virtual reality experience through a virtual reality headset worn by a user. For example, a passenger with chionophobia could wear a VR headset when the vehicle is being driven through snow. A driver could wear the VR headset to play a game or when the vehicle is in a stationary or parked configuration.

The controller 114 can instruct the user to utilize the CES system 132. Generally, CES is effective and safe for pain management and treatment of anxiety-related fear like chionophobia. It has no lasting side effects, no risk of addiction, and no danger of interaction with medications. CES devices deliver a natural level of micro-current, via small clips worn on a user's earlobe(s), through the brain to stimulate and modulate specific groups of nerve cells.

The micro-current can be millionths of an ampere. Treatments take generally about twenty minutes. CES generally leaves a user feeling both relaxed and alert. The effect differs from pharmaceutical treatments in that people report their body as feeling lighter and more relaxed and their mind, more alert and clearer. Results can be cumulative and lasting. And unlike drugs, CES has no negative side effects. It is non-addictive, and anyone can use it safely as often as they would like. A small pair of CES clips 134 can be provided in the vehicle 102. The CES clips can be connected to the CES 132 or another vehicle interface.

If any of the aforementioned interventions are insufficient, the controller 114 can allow a user to call emergency services through the HMI 118 or voice control service. The controller 114 can direct the user to the nearest parking venue for vehicle parking to await emergency services.

The user could alternatively select a ride-hail vehicle to be dispatched to their location. For example, the controller 114 can transmit a request to a ride-hail service 136 indirectly through the service provider 108 in some instances. The controller 114 can directly request service from the ride-hail service 136 in some instances. Additionally, the controller 114 can be configured to initiate a call to an individual on an emergency response list. For example, a user of a vehicle can specify a list of parties that can be called when either a one or two-stage intervention does not reduce a user's anxiety or fear. The controller 114 can utilize a telephonic or connectivity feature of the vehicle 102 to establish communications over, for example, a cellular or satellite network.

Figure 2:
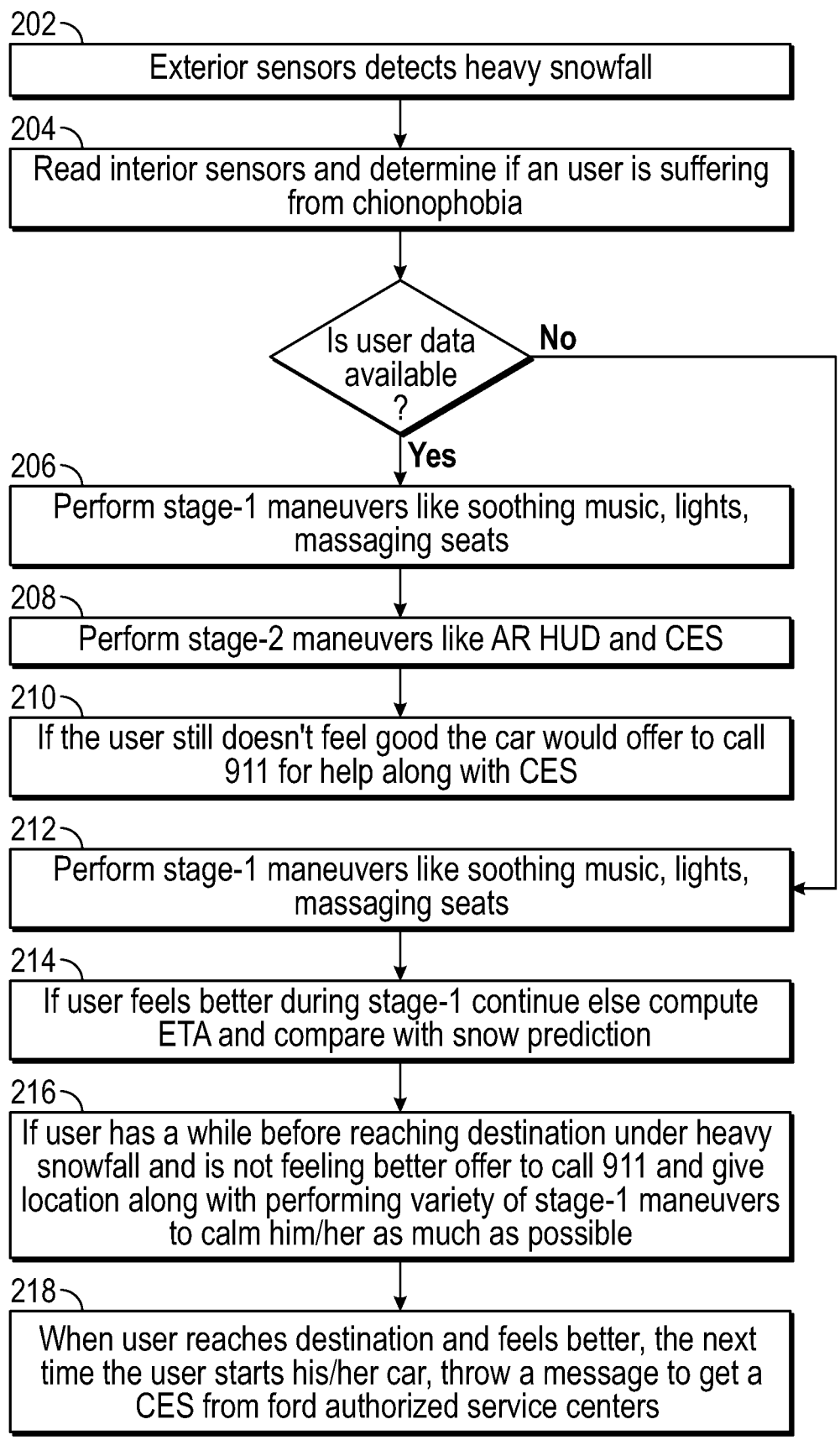
FIG. 2 is a flowchart of an example use case that utilizes the systems and methods disclosed herein.

FIG. 2 is a flowchart of an example use case of the present disclosure. The flowchart includes a step 202 of an exterior vehicle sensor detecting snowfall. This could include heavy snowfall or even presence of snowfall on a road based on prior snowfall. If snowfall is determined, the method can include a step 204 of reading interior sensors to determine if a user is suffering from chionophobia. If user data is available, the method can include a step 206 of performing stage one intervention maneuvers. Step 208 can include performing stage two intervention maneuvers. As noted above, stage two intervention maneuvers can occur if the user indicates that the stage one intervention maneuvers have not helped in reducing their anxiety or fear. In step 210, emergency responders or ride-hail services can be dispatched. Alternatively, CES, Augmented Reality (AR), or VR can be used along with emergency response or ride-hail service dispatch.

If user data is not available, the method can include a step 212 of performing stage one intervention maneuvers. Step 212 can occur if snowfall is determined or is likely to occur during a vehicle trip. If the user indicates that the stage one intervention maneuvers are reducing anxiety or fear due to chionophobia, the method can include a step 214 of computing an estimated time of arrival to a destination (if the user is using a navigation feature) and compare with a snowfall prediction (e.g., a determination that the vehicle may encounter snowfall during a trip).

When snowfall is detected and a time to the destination is above a threshold value, the method can include, the controller of the vehicle can offer to call 911 or dispatch a ride-hail service to a location of the user. The location can be determined from any suitable vehicle system such as GPS (global positioning system) signals in step 216. In some instances, information from a telematics control unit of the vehicle can be used. Step 216 can also be predicated upon no reduction in anxiety or fear by the stage one intervention maneuver(s). The vehicle can still continue to provide stage one or two interventions in some instances. When the user reaches their destination, the next time the vehicle is used, the controller can display a message through the vehicle HMI for the user to use or obtain a CES system in step 218. Other example instructional or educational messages or features can be provided as well. For example, the user can participate in a simulation using AR or VR, where the user can experience driving on snowfall in a simulated environment.

In addition to a negative user response, if the estimated time of arrival to the user's chosen destination is far, and if snow is predicted to fall heavily, the vehicle can provide the user with a choice to call emergency services or a ride-hail service with a vehicle location being sent automatically. As noted above, an alternative route can be determined and offered to the user that may route the vehicle around snowfall areas (if available).

Figure 3:
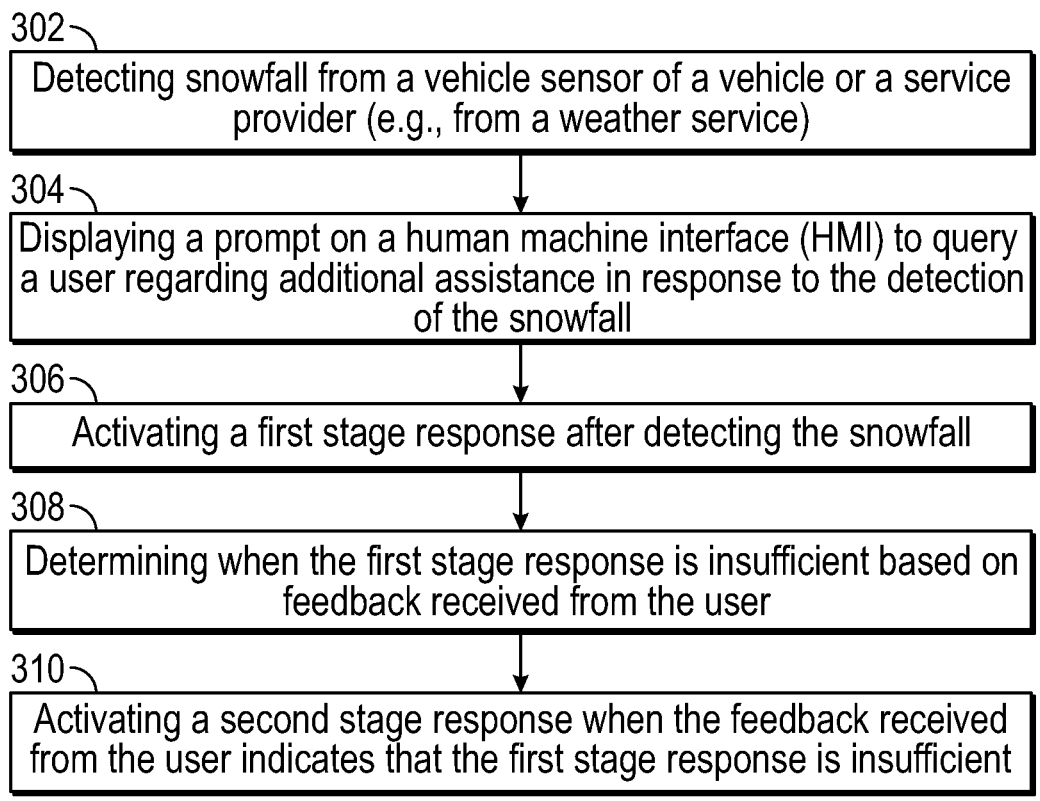
FIG. 3 is a flowchart of an example method of chionophobia intervention.

FIG. 3 is a flowchart of an example method of the present disclosure. The method includes a step 302 of detecting snowfall from a vehicle sensor of a vehicle or a service provider (e.g., from a weather service). The method can include a step 304 of displaying a prompt on a human machine interface (HMI) to query a user regarding additional assistance in response to the detection of the snowfall. The user can respond to the prompt with a voice response or by selecting a button provided on the HMI.

The method can include a step 306 of activating a first stage response after detecting the snowfall. The first stage response comprises at least one of activating a massage feature of a seat for the user, playing calming or humorous audio, displaying a calming or humorous scene on the HMI, providing a simulating game to enhance vehicle operation, or provide a reminder of safety features of the vehicle. The safety features comprise at least one of blind spot information system, adaptive cruise control, pre-collision assist with auto emergency braking, or adaptive headlights. Another first stage response comprises selectively adapting calibration of acceleration or braking of the vehicle. This can include damping response to brake pedal depression or damping response to throttle pedal input.

The method can include a step 308 of determining when the first stage response is insufficient based on feedback received from the user. The query could include an audible prompt or visual response provided on the HMI. The user can provide their response as a voice response or clicking a button provided on the HMI.

Figure 4:
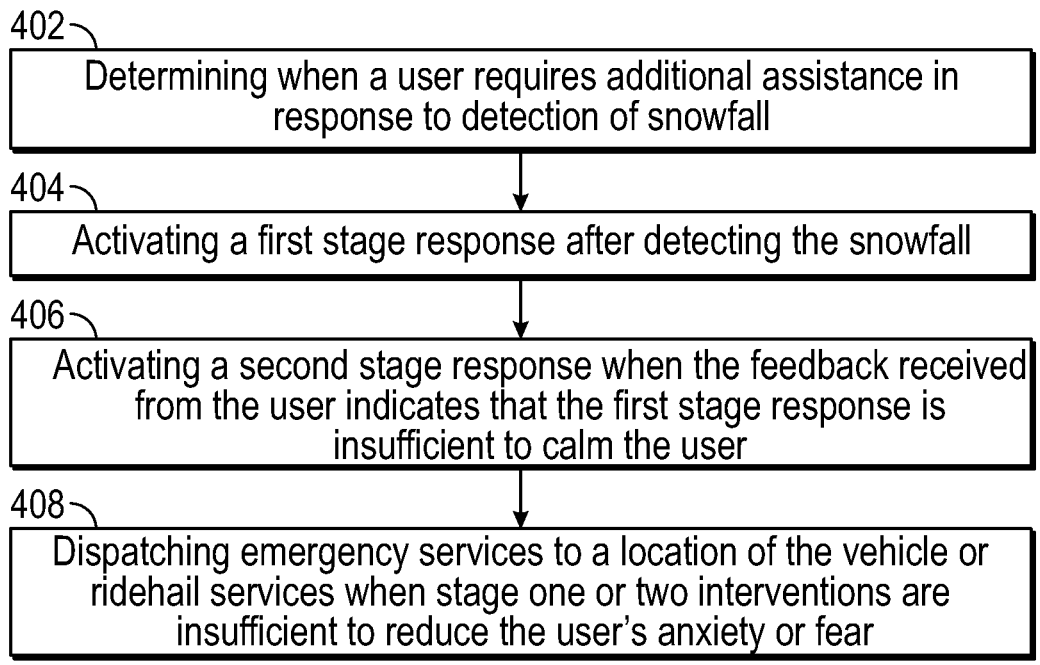
FIG. 4 is a flowchart of another example method of chionophobia intervention.

The method can include a step 310 of activating a second stage response when the feedback received from the user indicates that the first stage response is insufficient. A second stage response could comprise activating a heating element of a seat for the user, along with a massage feature of the seat. The second stage response could comprise displaying an augmented reality experience through a heads-up display of the vehicle. The augmented reality experience can include a projection of a road and traffic that obscures at least some of the snowfall. The second stage response can comprise providing cranial electrotherapy stimulation to the user. The second stage response can comprise dispatching a replacement driver to a location of the vehicle. FIG. 4 is another flowchart of an example method. The method can include a step 402 of determining when a user requires additional assistance in response to the detection of snowfall. This can include first determining that the user may experience chionophobia. This step could include displaying a prompt on a human-machine interface (HMI) to query a user regarding additional assistance in response to detection of snowfall. This display can be activated in response to detection of actual or perceived snowfall in the environment around the vehicle. The method can include a step 404 of activating a first stage response after detecting the snowfall, as well as a step 406 of activating a second stage response when feedback received from the user indicates that the first stage response is insufficient to calm the user. Whether the user is in a calm state can be determined based on biometric sensor output, camera image analysis of the user's face, blood pressure sensor, heart rate monitoring, voice analysis (e.g., detecting stress response from speech)—just to name a few. In other instances, calmness of the user can be determined from responses provided by the user to HMI prompts or audible questions.

For example, the first stage response is insufficient to calm the user when a biometric sensor associated with the vehicle determines that the user has at least one biometric reading that indicates that the user is experiencing stress. The method can also include a step 408 of dispatching emergency services to a location of the vehicle or ride-hail services when stage one or two interventions are insufficient to reduce the user's anxiety or fear.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiment.

Computer-executable instructions comprise, for example, instructions and data which, when executed at a processor, cause a general-purpose computer, special purpose computer, or special purpose processing device to perform a certain function or group of functions. The computer-executable instructions may be, for example, binaries, intermediate format instructions such as assembly language, or even source code. A "network" is defined as one or more data links that enable the transport of electronic data between computer systems and/or modules and/or other electronic devices. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the present disclosure may be practiced in network computing environments with many types of computer system configurations, including in-dash vehicle computers, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by any combination of hardwired and wireless data links) through a network, both perform tasks. In a distributed system environment, program modules may be located in both the local and remote memory storage devices.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein for purposes of illustration and are not intended to be limiting. Embodiments of the present disclosure may be implemented in further types of devices, as would be known to persons skilled in the relevant art(s).

What is claimed is:

1. A method, comprising:
   detecting snowfall from a vehicle sensor of a vehicle or from a service provider;
   displaying, based on detection of the snowfall, a prompt on a human machine interface (HMI) to query a user regarding additional assistance;
   activating, based on detection of the snowfall, a first stage response;
   determining that the user has chionophobia based on biometric identification obtained from the user, wherein the biometric identification is stored by the vehicle or a service provider, along with information that indicates that the user has chionophobia;
   determining, based on feedback received from the user, that the first stage response is insufficient; and
   activating, based on the feedback received from the user indicating that the first stage response is insufficient, a second stage response, wherein the second stage response comprises activating a heating element of a seat or a massage feature of the seat.

2. The method according to claim 1, wherein the first stage response comprises activating a massage feature of a seat for the user, playing calming or humorous audio, displaying a calming or humorous scene on the HMI, providing a simulating game to enhance vehicle operation, and/or providing a reminder of driver assist features of the vehicle.

3. The method according to claim 2, wherein the driver assist features comprise a blind spot information system, adaptive cruise control, pre-collision assist with auto emergency braking, and/or adaptive headlights.

4. The method according to claim 1, wherein the first stage response comprises selectively adapting calibration of acceleration or braking of the vehicle.

5. The method according to claim 1, wherein the second stage response comprises activating the heating element of the seat for the user, along with the massage feature of the seat.

6. The method according to claim 1, wherein the second stage response comprises displaying an augmented reality experience through a heads-up display of the vehicle, the augmented reality experience comprising a projection of a road and traffic that obscures at least some of the snowfall.

7. The method according to claim 1, wherein the second stage response comprises displaying a virtual reality experience through a virtual reality headset worn by the user or providing cranial electrotherapy stimulation to the user.

8. The method according to claim 1, wherein the second stage response comprises dispatching a replacement driver to a location of the vehicle or initiating a call to an individual on an emergency response list.

9. A system, comprising:
a vehicle sensor configured to sense snowfall;
a human machine interface (HMI) of the vehicle;
a processor; and
a memory for storing instructions, the processor executing the instructions to:
display a prompt on the HMI to query a user regarding additional assistance in response to detection of the snowfall;
activate a first stage response after detecting the snowfall;
determine when the first stage response is insufficient based on feedback received from the user, wherein the first stage response is insufficient to calm the user when a biometric sensor associated with the vehicle determines that the user has at least one biometric reading that indicates that the user is experiencing stress; and
activate a second stage response when the feedback received from the user indicates that the first stage response is insufficient, wherein the second stage response comprises activating a heating element of a seat or a massage feature of the seat.

10. The system according to claim 9, further comprising a seat of the vehicle occupied by the user, the seat being configured to emit heat and provide a massage feature, wherein the first stage response comprises the processor performing at least one of activating the massage feature, playing calming or humorous audio, displaying a calming or humorous scene on the HMI, providing a simulating game to enhance vehicle operation, or providing a reminder of driver assist features of the vehicle.

11. The system according to claim 10, wherein the driver assist features comprise a blind spot information system, adaptive cruise control, pre-collision assist with auto emergency braking, and/or adaptive headlights.

12. The system according to claim 9, wherein the first stage response comprises selectively adapting calibration of acceleration or braking of the vehicle.

13. The system according to claim 9, wherein the second stage response comprises at least one of:
displaying an augmented reality experience through a heads-up display of the vehicle, the augmented reality experience comprising a projection of a road and traffic that obscures at least some of the snowfall; or
displaying a virtual reality experience through a virtual reality headset worn by the user.

14. The system according to claim 9, wherein the second stage response comprises at least one of:
providing cranial electrotherapy stimulation to the user; or
dispatching a replacement driver or ride-hail service to a location of the vehicle.

15. The system according to claim 9, wherein the processor obtains information regarding the snowfall from a weather service over a network.

16. A method, comprising:
determining, in response to detection of snowfall, that a user of a vehicle requires additional assistance;
activating, based on detection of snowfall, a first stage response; and
activating, based on feedback received from the user indicating that the first stage response is insufficient to calm the user, a second stage response, wherein the first stage response is insufficient to calm the user when a biometric sensor associated with the vehicle determines that the user has at least one biometric reading that indicates that the user is experiencing stress, and wherein the second stage response comprises activating a heating element of a seat or a massage feature of the seat.

17. The method according to claim 16, further comprising receiving a response from the user that confirms when the user is experiencing stress.

18. The method according to claim 16, wherein the detection of snowfall is determined from a vehicle sensor or a weather service.

* * * * *